United States Patent
Wu et al.

(10) Patent No.: US 8,892,186 B2
(45) Date of Patent: *Nov. 18, 2014

(54) METHOD AND SYSTEM FOR DETECTION AND TRACKING OF CORONARY SINUS CATHETER ELECTRODES IN FLUOROSCOPIC IMAGES

(75) Inventors: Wen Wu, East Windsor, NJ (US); Terrence Chen, Princeton, NJ (US); Peng Wang, Princeton, NJ (US); Norbert Strobel, Heroldsbach (DE); Shaohua Kevin Zhou, Plainsboro, NJ (US); Dorin Comaniciu, Princeton, NJ (US)

(73) Assignee: Siemens Aktiengesellschaft, Munich (DE)

( * ) Notice: Subject to any disclaimer, the term of this patent is extended or adjusted under 35 U.S.C. 154(b) by 308 days.

This patent is subject to a terminal disclaimer.

(21) Appl. No.: 13/229,855

(22) Filed: Sep. 12, 2011

(65) Prior Publication Data

US 2012/0070046 A1    Mar. 22, 2012

Related U.S. Application Data

(60) Provisional application No. 61/384,388, filed on Sep. 20, 2010.

(51) Int. Cl.
| | | |
|---|---|---|
| *A61B 5/05* | (2006.01) | |
| *G06T 7/00* | (2006.01) | |
| *G06T 7/20* | (2006.01) | |
| *A61B 19/00* | (2006.01) | |

(52) U.S. Cl.
CPC ............... *G06T 7/0014* (2013.01); *G06T 7/20* (2013.01); *A61B 2019/5238* (2013.01); *A61B 2019/5265* (2013.01); *G06K 2209/057* (2013.01); *G06T 2207/10121* (2013.01); *G06T 2207/30021* (2013.01); *G06T 2207/30048* (2013.01)
USPC .................................................. 600/424

(58) Field of Classification Search
USPC ........................................................ 600/424
See application file for complete search history.

(56) References Cited

U.S. PATENT DOCUMENTS

| | | | |
|---|---|---|---|
| 7,792,342 B2 | 9/2010 | Barbu et al. | |
| 2003/0014034 A1* | 1/2003 | Strobel ......................... | 604/407 |
| 2003/0235337 A1* | 12/2003 | Paragios et al. ............... | 382/215 |
| 2004/0024309 A1* | 2/2004 | Ferre et al. .................. | 600/424 |
| 2005/0152617 A1* | 7/2005 | Roche et al. ................. | 382/294 |
| 2007/0189580 A1* | 8/2007 | Slabaugh et al. ............. | 382/103 |
| 2007/0270692 A1* | 11/2007 | Barbu et al. .................. | 600/431 |
| 2008/0080754 A1 | 4/2008 | Barbu et al. | |
| 2008/0317317 A1* | 12/2008 | Shekhar et al. ............... | 382/131 |
| 2009/0062641 A1* | 3/2009 | Barbu et al. .................. | 600/424 |
| 2009/0163800 A1* | 6/2009 | Xu et al. ....................... | 600/424 |
| 2009/0279767 A1 | 11/2009 | Kukuk et al. | |
| 2010/0121181 A1 | 5/2010 | Wang et al. | |
| 2011/0122226 A1* | 5/2011 | Kamen et al. ................. | 348/43 |

\* cited by examiner

*Primary Examiner* — Jonathan Cwern
*Assistant Examiner* — Amelie R Gillman

(57) ABSTRACT

A method and system for detecting and tracking coronary sinus (CS) catheter electrodes in a fluoroscopic image sequence is disclosed. An electrode model is initialized in a first frame of the fluoroscopic image sequence based on input locations of CS sinus catheter electrodes in the first frame. The electrode model is tracked in subsequent frames of the fluoroscopic image sequence by detecting electrode position candidates in the subsequent frames of the fluoroscopic image sequence using at least one trained electrode detector, generating electrode model candidates in the subsequent frames based on the detected electrode position candidates, calculating a probability score for each of the electrode model candidates, and selecting an electrode model candidate based on the probability score.

38 Claims, 7 Drawing Sheets

500 510 520

METHOD AND SYSTEM FOR DETECTION AND TRACKING OF CORONARY SINUS CATHETER ELECTRODES IN FLUOROSCOPIC IMAGES

This application claims the benefit of U.S. Provisional Application No. 61/384,388, filed Sep. 20, 2010, the disclosure of which is herein incorporated by reference.

BACKGROUND OF THE INVENTION

The present invention relates to detection and tracking of coronary sinus catheter electrodes in fluoroscopic images, and more particularly, to detecting and tracking coronary sinus catheter electrodes in fluoroscopic images to assist in atrial fibrillation ablation procedures.

Atrial fibrillation (Afib) is a rapid, highly irregular heartbeat caused by abnormalities in the electrical signals generated by the atria of the heart. It is the most common cardiac arrhythmia (abnormal heart rhythm) and involves the two upper chambers (atria) of the heart. Afib can often be identified by taking a pulse and observing that the heartbeats do not occur at regular intervals. However, a stronger indicator of Afib is the absence of P waves on an electrocardiogram, which are normally present when there is a coordinated atrial contraction at the beginning of each heart beat. Afib may be treated with medications that either slow the heart rate or revert the heart rhythm back to normal, but this treatment may be difficult and result in complications if a patient has other diseases. Synchronized electrical cardioversion may also be used to convert Afib to a normal heart rhythm, but this technique is rarely used. Surgical and catheter-based Afib therapies, such as an ablation procedure, are also commonly used to treat Afib.

The identification of triggers that initiate Afib within the pulmonary veins (PVs) has led to prevention of Afib recurrence by catheter ablation at the site of origin of the trigger. Direct catheter ablation of the triggers was traditionally limited by the infrequency with which Afib initiation could be reproducibly triggered during a catheter ablation procedure. To overcome these limitations, an ablation approach was introduced to electrically isolate the PV myocardium. This segmental PV isolation technique involved the sequential identification and ablation of the PV ostium close to the earliest sites of activation of the PV musculature. This typically involved the delivery of radio frequency (RF) energy to 30% to 80% of the circumference of the PVs. The endpoint of this procedure was the electrical isolation of at least three PVs.

In order to construct an electrical map of the heart and assist a radiofrequency ablation operation, different catheters are inserted in a blood vessel in a patient's arm or leg and guided to the heart. The entire operation can be monitored with real-time fluoroscopic images. Tracking electrodes of the coronary sinus (CS) catheter (the catheter inside the CS) has been shown to be effective to compensate respiratory and cardiac motion for 3D overlay to assist physicians when positioning the ablation catheter. However, conventional tracking algorithms encounter difficulties in the presence of large image variations, nearby similar structures, and cluttered background.

BRIEF SUMMARY OF THE INVENTION

Embodiments of the present invention provide a robust and fast learning-based approach to automatically detect and track coronary sinus (CS) catheter electrodes on continuous mono-plane and bi-plane fluoroscopic image sequences to assist in atrial fibrillation (Afib) treatment using ablation procedures. Embodiments of the present invention utilize a flexible learning-based algorithm to localize and track CS catheter electrodes in each frame of a fluoroscopic image sequence. Embodiments of the present invention are robust and flexible enough to track the CS catheters with few electrodes and with many electrodes when deformation and motion are constantly present.

In one embodiment of the present invention, a catheter electrode model is initialized in a first frame of a fluoroscopic image sequence based on input locations a plurality of CS sinus catheter electrodes in the first frame. The catheter electrode model is tracked in a second frame of the fluoroscopic image sequence by detecting electrode position candidates in a second frame of the fluoroscopic image sequence using a trained electrode detector, generating catheter electrode model candidates in the second frame based on the detected electrode position candidates, calculating a probability score for each of the catheter electrode model candidates, and selecting one of the catheter electrode model candidates based on the probability score. The selected catheter electrode model candidate provides locations of the plurality of CS sinus catheter electrodes in the second frame.

These and other advantages of the invention will be apparent to those of ordinary skill in the art by reference to the following detailed description and the accompanying drawings.

DETAILED DESCRIPTION

The present invention relates to a method and system for detecting and tracking coronary sinus (CS) catheter electrodes in fluoroscopic images. Embodiments of the present invention are described herein to give a visual understanding of the CS catheter electrode detection and tracking method. A digital image is often composed of digital representations of one or more objects (or shapes). The digital representation of an object is often described herein in terms of identifying and manipulating the object. Such manipulations are virtual manipulations accomplished in the memory or other circuitry/hardware of a computer system. Accordingly, is to be understood that embodiments of the present invention may be performed within a computer system using data stored within the computer system.

Figure 1:
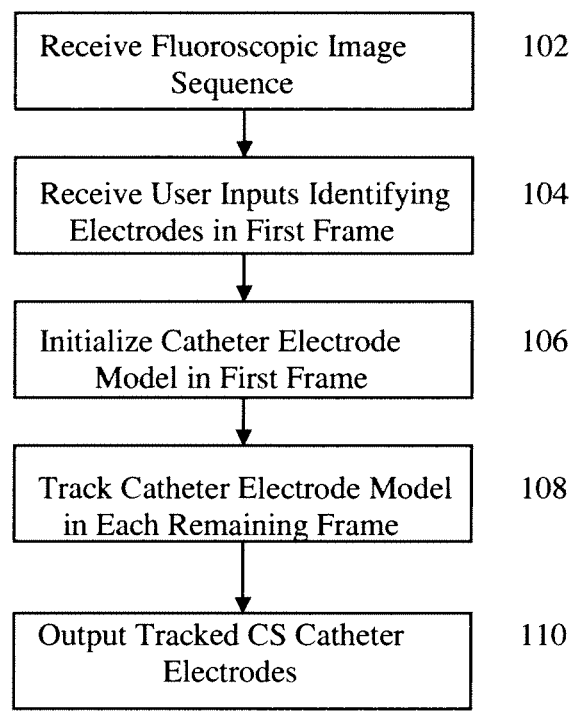
FIG. 1 illustrates a method for detecting and tracking CS catheter electrodes in a fluoroscopic image sequence according to an embodiment of the present invention.

FIG. 1 illustrates a method for detecting and tracking CS catheter electrodes in a fluoroscopic image sequence according to an embodiment of the present invention. As illustrated in FIG. 1, at step 102, a fluoroscopic image sequence is received. The fluoroscopic image sequence is a sequence of fluoroscopic (x-ray) images acquired over a time period. The fluoroscopic image sequence can be received directly from an x-ray imaging device. It is also possible that the fluoroscopic image sequence can be received by loading a previously stored fluoroscopic image sequence.

At step 104, user inputs are received identifying locations of CS catheter electrodes in a first frame of the fluoroscopic image sequence. In particular, using a computer input device, such as a mouse, a user can click on the locations the CS catheter electrodes in the first frame of the fluoroscopic image sequence. At step 106, a CS catheter electrode model is initialized in the first frame based on the user input locations of the CS catheter electrodes. The CS catheter electrode model initialized in the first frame is then used to detect the locations of the CS catheter electrodes in each remaining frame of the fluoroscopic image sequence.

Figure 2:
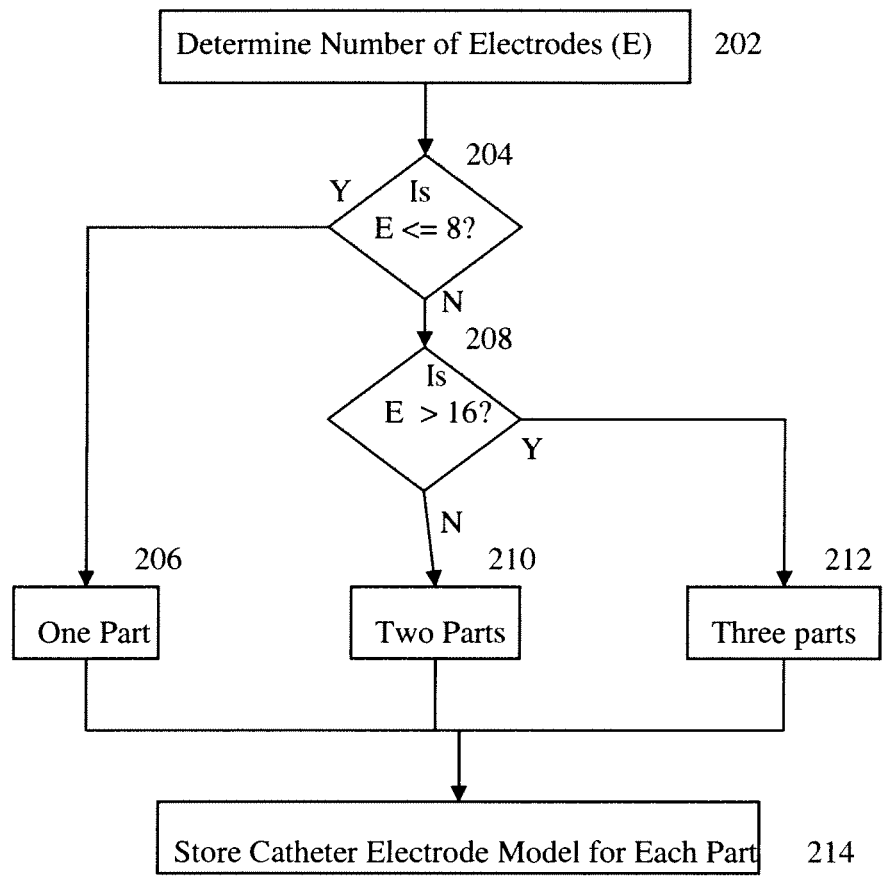
FIG. 2 illustrates a method for initializing the CS catheter electrode model in the first frame of the fluoroscopic image sequence according to an embodiment of the present invention.

FIG. 2 illustrates a method for initializing the CS catheter electrode model in the first frame of the fluoroscopic image sequence according to an embodiment of the present invention. The method of FIG. 2 can be used to implement step 106 of FIG. 1. As illustrated in FIG. 2, at step 202, a number of CS catheter electrodes (E) is determined based on the user input locations of the CS catheter electrodes. At step 204, it is determined whether there are less than or equal to eight electrodes identified in the first frame. If there are less than or equal to eight electrodes, the method proceeds to step 206. If there are more than eight electrodes, the method proceeds to step 208. At step 206, if there are less than or equal to eight electrodes, it is determined that a single part electrode model is used. At step 208, it is determined whether there are greater than 16 electrodes identified in the first frame. If there are not more than 16 electrodes, the method proceeds to step 210. If there are more than 16 electrodes, the method proceeds to step 212. At step 210, if there are more than eight and less than or equal to 16 electrodes, the electrodes are decomposed into two parts. At step 212, if there are more than 16 electrodes, the electrodes are decomposed into three parts.

The decomposition of the identified electrodes into two or three parts in steps 210 and 212 is based on a curvature analysis along the CS catheter shape, which is a spline formed by the identified electrodes. In one possible implementation, the highest curvature points on the spline can be selected as points to divide the spline into multiple parts. It is also possible to constrain the decomposition of the electrodes into multiple parts based on the locations of the electrodes in the first frame to ensure that the electrodes are divided relatively evenly between the parts.

At step 214, a catheter electrode model is stored for each part based on the input electrode locations. In particular, for each part, the coordinates of the CS catheter template and the corresponding intensity values for each point in the first frame of the fluoroscopic image sequence in which the user clicks electrodes are stored by densely sampling points in normal directions along the spline constructed by the user input electrode center points. An electrode mask is also constructed for each part based on the relative locations of the electrodes. The electrode mask facilitates summing up electrode detection scores at individual electrode locations during tracking. In cases in which electrode models are stored for multiple parts, the electrode models can be ordered, for example from the catheter tip to the proximal electrode.

Returning to FIG. 1, at step 108, the CS catheter electrode model that is initialized in the first frame is tracked in each remaining frame of the fluoroscopic image sequence. The catheter electrode model, which may be a single part model or a multiple part model, is tracked by a hypothesis fusion framework and using learning-based electrode detection to generate model candidates.

Figure 3:
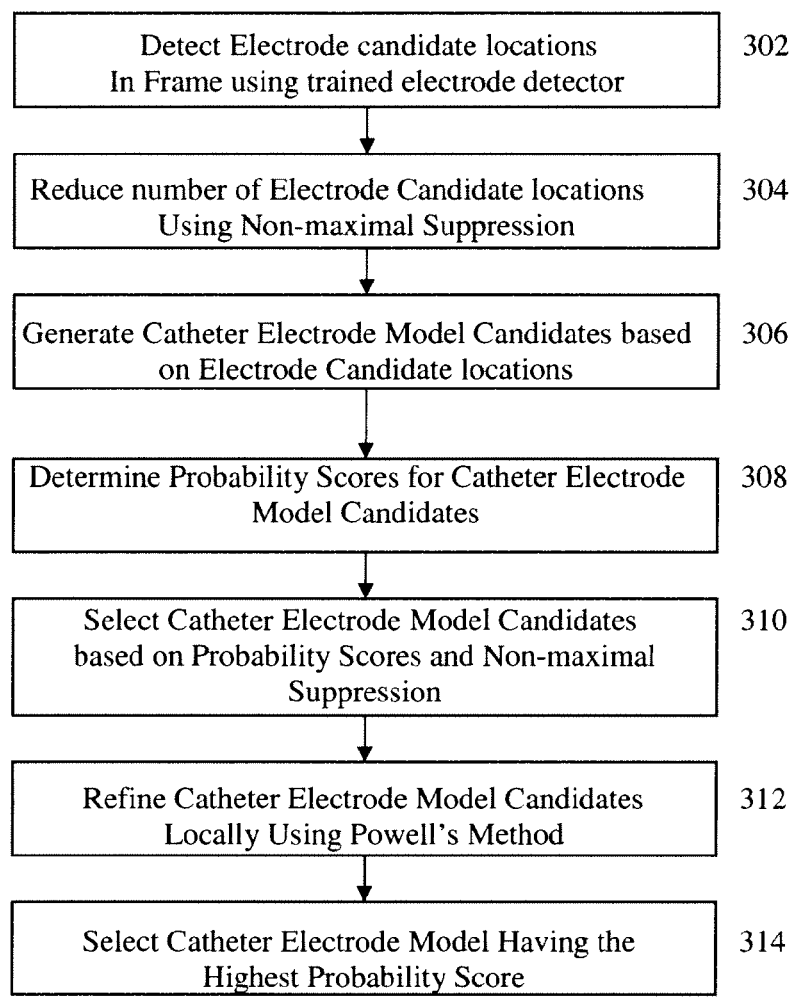
FIG. 3 illustrates a method for tracking a single-part CS catheter electrode model in a frame of a fluoroscopic image sequence according to an embodiment of the present invention.

FIG. 3 illustrates a method for tracking a single-part CS catheter electrode model in a frame of a fluoroscopic image sequence in order to detect the CS catheter electrodes in that frame according to an embodiment of the present invention. The method of FIG. 3 can be repeated for each remaining frame of the fluoroscopic image sequence to implement step 108 of FIG. 1 in cases for which the CS catheter electrode model initialized in the first frame has a single part.

As illustrated in FIG. 3, at step 302, electrode candidate locations are detected in a frame of the fluoroscopic image sequence using a trained electrode detector. Electrode detection can be formulated as an object detection framework to solve a two-class (object vs. background) classification problem. A box is used to scan the image to extract candidate samples. Each sample is fed to the trained electrode detector to obtain a probability score of being a CS catheter electrode. For individual electrodes, the location parameter space has two parameters, x and y. According to an advantageous implementation, a box based representation is used, in which a box (e.g., 69×69 pixels) is centered at a candidate sample, in order to include both electrodes and their context.

According to an embodiment of the present invention, a probabilistic boosting tree (PBT) can be used as the core machine learning algorithm to train the electrode detector. The detector is a tree-based structure with which the posterior probabilities of the presence of the electrodes are calculated from given image data. Accordingly, the trained electrode detector not only provides a binary decision for a given sample but also a confidence value associated with the decision. The nodes of in the tree are constructed by a non-linear combination of simple classifiers using boosting techniques.

Figure 4:
FIG. 4 illustrates exemplary Haar wavelet-like features.

Each electrode detector selects a set of discriminative features that are used to distinguish the positive (electrode) locations from the negatives (background and other structures) from a large pool of features. Different parameter space utilizes different features calculated from image data. For individual electrode detectors, Haar wavelet-like features can be used. FIG. 4 illustrates exemplary Haar wavelet-like features.

According to an advantageous implementation, the electrode detection may be performed using multiple trained electrode detectors. For example, a bootstrapping strategy can be used to effectively remove false positive detections. In this case, there are two stages of trained detectors for individual electrode detection. The first stage detector is trained using annotated training data with target electrodes used as positive training samples and randomly selected negative training samples. The second stage detector is trained using the target electrodes as the positive training samples and false positives detected by the first stage detector as negative training samples. The first stage is used to quickly remove negative samples and the second stage is aimed at pruning out more confusing or difficult samples that may result in false positives. After detection using the first and second stage detectors, the detection results can be clustered into electrode candidate locations using non-maximal suppression.

Figure 5:
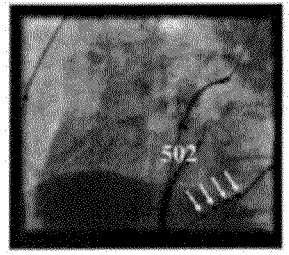
FIG. 5 illustrates exemplary electrode candidate detection results.
Figure 5:
Figure 5:
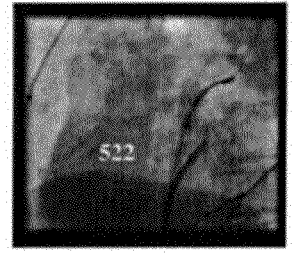

FIG. 5 illustrates exemplary electrode candidate detection results. As illustrated in FIG. 5, image 500 shows the locations of target electrodes 502 in an input image. Image 510 shows electrode positions 512 automatically detected using the PBT-based electrode detectors. Image 520 shows electrode candidate positions 522 after non-maximal suppression. These electrode candidate positions can then be used to generate catheter electrode model tracking hypotheses.

At step 304, the number of electrode candidates is reduced using non-maximal suppression. Non-maximal suppression is a well-known technique that can be used to cluster detection results. This combines multiple candidates that are close together and should be considered as the same candidate.

Returning to FIG. 3, at step 306, electrode model candidates are generated based on the electrode candidate positions detected in step 304. In particular, for each of K electrode candidate positions detected in step 304, E (the number of electrodes) electrode model hypotheses are generated by translating each electrode in the electrode model to each respective electrode candidate position. This results in K*E electrode model hypotheses. A set of electrode model candidates is generated for each catheter electrode model hypothesis by applying an affine transformation of the catheter electrode model candidate by varying translation (Tx, Ty), scale (Sx, Sy), rotation (R), and skew (Sk). This results in a large number of catheter electrode model candidates (tracking hypotheses), each of which is a complete set of coordinates corresponding to locations of all of template points in the catheter electrode model.

At step 308, a probability score is determined for each of the electrode model candidates. The probability score is based on a comparison of the intensity values of the electrodes in the catheter electrode model hypothesis and the electrode model initialized in the first frame, as well as the detection scores for the electrodes in the model hypothesis using the trained electrode detector. In particular, the probability (confidence) score for each catheter electrode model candidate can be expressed as:

$$P(C|M_i)=P_{Img}(C|M_i) \cdot P_{Det}(C|M_i)$$

where C denotes the CS catheter and $M_i$ denotes the i-th candidate model. $P_{Img}(C|M_i)$ is the matching score given image intensity evidence and computed by normalized cross correlation between the intensity values of the template points in the candidate model and the intensity values of the template points in the electrode model initialized in the first frame. $P_{Det}(C|M_i)$ represents the probability value given by electrode detection scores for the electrodes in the candidate model. The stored electrode mask for the initialized electrode model can be placed on the current frame using the affine parameters [Tx, Ty, Sx, Sy, R, Sk] of the current candidate model. The trained electrode detector can then calculate the probability of being an electrode for each electrode location given by the electrode mask. The probabilities of each electrode can be summed to calculate $P_{Det}(C|M_i)$.

Alternatively, the probability (confidence) score for each catheter electrode model candidate can also be expressed as:

$$P(C|M_i)=(1-a) \cdot P_{Img}(C|M_i)+a \cdot P_{Det}(C|M_i)$$

where a is a weight whose value is between 0 and 1, and it can also be defined as $a=1/(1+e^{-P_{Img}(C|M_i)})$. Both score calculations shown in above equations have been implemented by the present inventors and are effective.

At step 310, a number of catheter electrode model candidates are selected having the highest probability scores. For example, a predetermined number of electrode model candidates having the highest probability scores may be selected. Alternatively, all catheter electrode model candidates having a probability score over a certain threshold may be selected. It is also possible that a predetermined number of catheter electrode model candidates having the highest probability scores over a certain threshold are selected. In an advantageous implementation, non-maximal suppression can be used to reduce the number of catheter electrode model candidates prior to selecting the catheter electrode model candidates having the highest scores.

At step 312, the selected electrode model candidates are refined to find the local maximum probability score for each candidate. In order to refine matching locally, Powell's method can be applied to find the local maximum probability score. Powell's method utilizes a bidirectional search along a search vector for each affine parameter in turn to maximize a candidate model's probability score. This is repeated a certain number of times or until the method converges and no further improvement is possible. This can achieve minor adjustments in the affine parameters of a candidate model that result in an improved probability score.

At step 314, a catheter electrode model is detected in the frame by selecting the catheter electrode model candidate having the highest probability score. This catheter electrode model candidate gives the locations of all of the electrodes in the frame.

Figure 6:
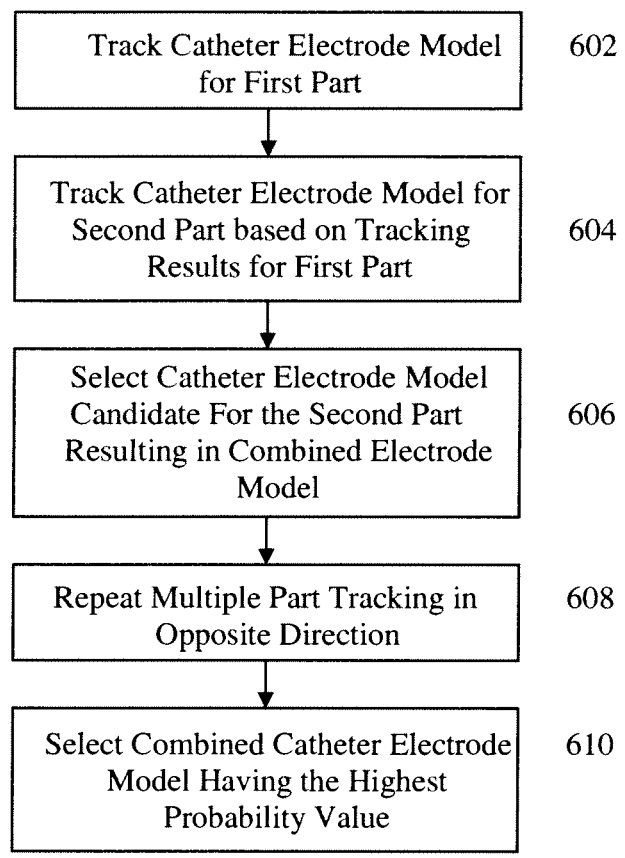
FIG. 6 illustrates a method for tracking a multiple-part CS catheter electrode model in a frame of a fluoroscopic image sequence according to an embodiment of the present invention.

FIG. 6 illustrates a method for tracking a multiple-part CS catheter electrode model in a frame of a fluoroscopic image sequence in order to detect the CS catheter electrodes in that frame according to an embodiment of the present invention. The method of FIG. 6 can be repeated for each remaining frame of the fluoroscopic image sequence to implement step 108 of FIG. 1 in cases for which the CS catheter electrode model initialized in the first frame has multiple parts.

As illustrated in FIG. 6, at step 602, the CS catheter electrode model for a first part is tracked in the frame to generate one or more candidate electrode models for the first part. The method of FIG. 3 described above can be used to track the electrode model for the first part in the frame. In one possible implementation, steps 302-314 can be performed for the electrode model for the first part, resulting in a single electrode candidate model for the first part having the highest probability score. In another possible implementation, in order to generate a larger number of hypotheses for the second part, steps 302-312 can be performed for the electrode model for the first part, resulting in a number of electrode candidate models for the first part having the highest probability scores.

At step 604, the catheter electrode model in the second part is tracked based on the catheter electrode model tracking results for the previous part. Catheter electrode model hypotheses for the second part are generated based on each of the electrode model candidates detected for the first part. Adjacent parts share an electrode. That is the last electrode of the first part will be the first electrode of the second part. For tracking the second part, the last electrode of the first part is fed to the tracking algorithm as the rotation center. Accordingly, electrode model hypotheses for the second part can be generated by placing the first electrode of the electrode model for the second part at the last electrode for each electrode model candidate detected for the first part and varying the affine parameters. Once the electrode model hypotheses/candidates for the second part are generated, steps 306-312 are performed for the electrode model candidates for the second part.

At step 606, a catheter electrode model candidate for the second part is selected which gives the greatest combined probability score for the first and second parts. This results in a combined electrode model for the first and second part. It is to be understood that steps 604 and 606 can be repeated for a third part, for which candidate models are generated based on the last electrode in the electrode model candidate selected for the second part.

At step 608, the multiple part tracking is repeated in the opposite direction. That is steps 602-606 are repeated in the opposite direction. For example, if the parts were originally tracked in a direction from the catheter tip to the proximal electrode, the tracking is repeated but the second time the tracking is performed from the proximal electrode to the catheter tip. That is, if there are two parts, at step 608, the electrode model for the second part is tracked first and the electrode model for the first part is then tracked based on the tracking results for the second part. This results in another combined electrode model for all of the parts.

At step 610, combined electrode model having the highest probability score is selected as the electrode model for the frame. The probability scores for the first combined electrode model resulting from tracking in the first direction and the second combined electrode model resulting from tracking in the second direction are compared. The combined electrode model having the highest probability score is selected and provides detection results for all of the electrodes in the frame.

Returning to FIG. 1, at step 110, the tracked CS catheter electrodes are output. Once the CS catheter electrodes are detected in each frame of the fluoroscopic image sequence, the tracked CS catheters can be output, for example, by displaying the locations of the CS catheters on the fluoroscopic images or saving the tracked locations in a memory or storage of a computer system. In one embodiment, the CS catheters can be tracked and displayed in real-time on the fluoroscopic images in order to assist in an Afib ablation procedure.

The methods described above can be implemented to track catheter electrodes in original resolution, half resolution, or multi-resolution. In one possible implementation, for catheters with eight electrodes or less, the tracking can be performed on half resolution and Powell's method can be performed on the original resolution. For catheters with nine electrodes or more, the tracking and Powell's method can both be performed on half-resolution.

The above described methods can be utilized for CS catheter electrode tracking in mono-plane or bi-plane fluoroscopic image sequences. When applied to bi-plane fluoroscopic image sequences, the methods above can be separately applied to each of sequence, and the tracking results for the two sequences can be combined.

The present inventors conducted experiments using 658 DICOM sequences recording Afib procedures from 23 different patient cases to construct an evaluation database. 1663 frames of 498 sequences (7614 frames) were annotated to build an evaluation database (sequences are not included in evaluation because they either do not include a CS catheter or just 1-frame sequences). Original image resolutions range from 0.1725 to 0.183 mm/pixel. Electrode detectors were trained on 256*256, 512*512 and 1024*1024 resolutions using 1518 frames (419 of which are from another catheter dataset) and frames were normalized to 0.366 mm/pixel for tracking.

For evaluation, the tracking method was initialized by the first-available-frame annotation and the tracking method tracks catheter electrodes in a fully automatic fashion. Euclidean distance is computed between the tracked electrode position and its ground truth counterpart as the tracking error for each electrode. The average distance error of all CS catheter electrodes in a frame is used as the metric to evaluate performance of the tracking method.

Performance of the tracking method on the CS catheter dataset is summarized in Table 1 below. Distance errors are reported in millimeters. All frame errors in the evaluation set are sorted in ascending order and the errors are reported at percentile 75 (P75), 80, 85, 90, 95. As shown in Table 1, the tracking method, according to an embodiment of the present invention, achieves mean error 1.0 mm, median error 0.52 mm, 95 percent of frames have less than or equal to 1.0 mm error. The speed of the tracking method reaches 12-15 frames-per-second depending on the number of electrodes on the catheter and the length of the catheter segment with the electrodes.

TABLE 1

| Frames | Electrode number | Mean error (mm) | Median error (mm) | P75 (mm) | P80 (mm) | P85 (mm) | P90 (mm) | P95 (mm) |
|---|---|---|---|---|---|---|---|---|
| 1663 | 7014 | 1.0 | 0.52 | 0.6 | 0.7 | 0.7 | 0.8 | 1.0 |

Figure 7:
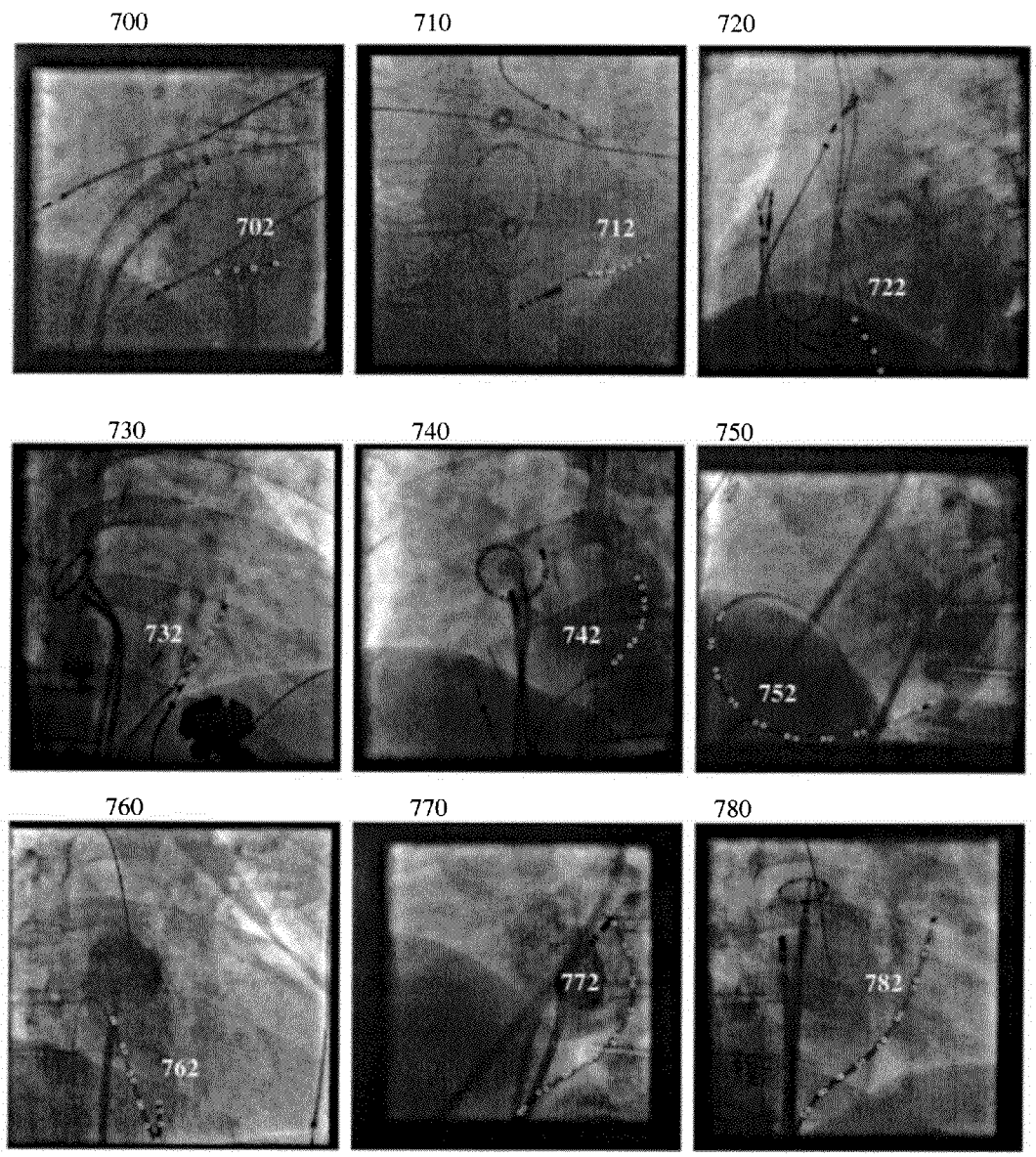
FIG. 7 shows examples of CS catheter electrode tracking results.

FIG. 7 shows examples of CS catheter electrode tracking results. As illustrated in FIG. 7, images 700, 710, 720, 730, 740, 750, 760, 770, and 780 show CS catheter electrodes 702, 712, 722, 732, 742, 752, 762, 772, and 782, respectively, detected using the methods described in above in FIGS. 1, 2, 3, and 6. As shown in FIG. 7, the CS catheter electrode detection and tracking method described above can successfully track CS catheters with different number of electrodes in presence of complex background, motions and deformations.

Figure 8:
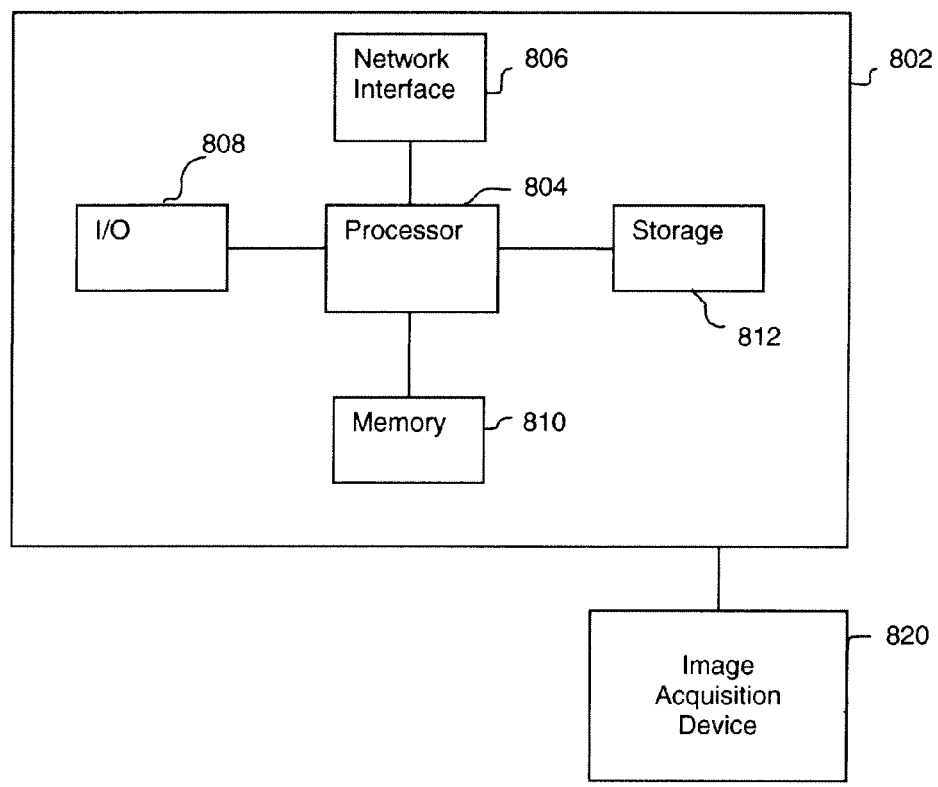
FIG. 8 is a high level block diagram of a computer capable of implementing the present invention.

The above-described methods for CS catheter electrode detection and tracking in a fluoroscopic image sequence may be implemented on a computer using well-known computer processors, memory units, storage devices, computer software, and other components. A high level block diagram of such a computer is illustrated in FIG. 8. Computer 802 contains a processor 804 which controls the overall operation of the computer 802 by executing computer program instructions which define such operation. The computer program instructions may be stored in a storage device 812, or other computer readable medium, (e.g., magnetic disk) and loaded into memory 810 when execution of the computer program instructions is desired. Thus, all method steps described above, including the method steps illustrated in FIGS. 1, 2, 3, and 6 may be defined by the computer program instructions stored in the memory 810 and/or storage 812 and controlled by the processor 804 executing the computer program instructions. An image acquisition device 820, such as an X-ray imaging device, can be connected to the computer 802 to input fluoroscopic image sequences to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.) One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for detecting and tracking coronary sinus (CS) catheter electrodes in a fluoroscopic image sequence comprising:
    initializing a catheter electrode model in a first frame of a fluoroscopic image sequence based on input locations of a plurality of CS catheter electrodes in the first frame, wherein the catheter electrode model in the first frame comprises a plurality of template points corresponding to locations of the CS catheter electrodes in the first frame; and
    tracking the catheter electrode model in a second frame of the fluoroscopic image sequence by:
        detecting electrode position candidates in a second frame of the fluoroscopic image sequence using at least one trained electrode detector;
        generating catheter electrode model candidates in the second frame based on the detected electrode position candidates and the catheter electrode model initialized in the first frame by translating each of the plurality of template points of the catheter electrode model initialized in the first frame to each of the detected electrode position candidates in the second frame;
        calculating a probability score for each of the catheter electrode model candidates in the second frame; and
        selecting one of the catheter electrode model candidates in the second frame based on the probability score, wherein the selected catheter electrode model candidate provides locations of the plurality of CS catheter electrodes in the second frame.

2. The method of claim 1, wherein the step of initializing a catheter electrode model in a first frame of a fluoroscopic image sequence based on input locations of a plurality of CS catheter electrodes in the first frame comprises:
    storing coordinates of the template points based on the plurality of CS catheter electrodes in the first frame and intensity information corresponding to each template point based on the plurality of CS catheter electrodes in the first frame.

3. The method of claim 1, wherein the step of initializing a catheter electrode model in a first frame of a fluoroscopic image sequence based on input locations of a plurality of CS catheter electrodes in the first frame comprises:
    determining a number of CS catheter electrodes in the first frame; and
    if the number of CS catheter electrodes in the first frame is greater than a threshold,
        decomposing the plurality of CS catheter electrodes into multiple parts, and
        initializing separate catheter electrode models in the first frame for the multiple parts, wherein the catheter electrode model initialized in the first frame comprises the separate catheter electrode models initialized for the multiple parts.

4. The method of claim 3, wherein the step of decomposing the plurality of CS catheter electrodes into multiple parts comprises:
    splitting the CS catheter electrodes into multiple parts based on curvature of a spline representing the CS catheter.

5. The method of claim 3, wherein the threshold is eight, and the step of decomposing the plurality of CS catheter electrodes into multiple parts comprises:
    if the number of CS catheter electrodes in the first frame is greater than 16, decomposing the plurality of CS catheter electrodes into three parts; and
    if the number of CS catheter electrodes in the first frame is less than or equal to than 16, decomposing the plurality of CS catheter electrodes into two parts.

6. The method of claim 1, wherein the at least one trained electrode detector is a probabilistic boosting tree detector trained based on annotated training data using Haar wavelet-like features.

7. The method of claim 1, wherein the step of detecting electrode position candidates in a second frame of the fluoroscopic image sequence using at least one trained electrode detector comprises:
    detecting a first set of electrode position candidates in the second frame using a first trained electrode detector;
    detecting a second set of electrode position candidates by pruning the first set of electrode position candidates using a second trained electrode detector; and
    clustering the second set of electrode position candidates using non-maximal suppression.

8. The method of claim 1, wherein the step of generating catheter electrode model candidates in the second frame based on the detected electrode position candidates and the catheter electrode model initialized in the first frame by translating each of the plurality of template points of the catheter electrode model initialized in the first frame to each of the detected electrode position candidates in the second frame comprises:
    generating a plurality of catheter electrode model hypotheses by translating each of the plurality of template points of the catheter electrode model initialized in the first frame to each of the detected electrode position candidates in the second frame; and
    generating the plurality of catheter electrode model candidates in the second frame by varying affine parameters for each of the plurality of catheter electrode model hypotheses using the respective detected electrode position candidate as a transformation center.

9. The method of claim 1, wherein the step of calculating a probability score for each of the catheter electrode model candidates in the second frame comprises:
    calculating a probability score based on a first probability score and a second probability score,
    wherein the first probability score is calculated by normalized cross correlation between intensity values of template points in the second frame identified by the respective catheter electrode model candidate and the intensity values of the template points in the first frame identified by the catheter electrode model, and
    the second probability score is calculated based on detection scores of the electrodes identified by the respective catheter electrode model candidate determined by the at least one trained electrode detector, wherein the electrodes identified by the respective catheter electrode model candidate are identified in the second frame using an electrode mask derived from the template points in the first frame.

10. The method of claim 1, wherein the step of selecting one of the catheter electrode model candidates in the second frame based on the probability score comprises:

selecting a number of catheter electrode model candidates in the second frame based on the probability scores calculated for the catheter electrode model candidates in the second frame;

refining affine parameters of the selected catheter electrode model candidates in the second frame to locally maximize the probability scores; and selecting the catheter electrode model candidate in the second frame having the highest locally maximized probability score.

11. The method of claim 10, wherein the step of selecting one of the catheter electrode model candidates in the second frame based on the probability score further comprises:

clustering the catheter electrode model candidates in the second frame using non-maximal suppression prior to the step of selecting a number of catheter electrode model candidates in the second frame based on the probability scores calculated for the catheter electrode model candidates.

12. The method of claim 10, wherein the step of refining affine parameters of the selected catheter electrode model candidates in the second frame to locally maximize the probability scores comprises:

refining the affine parameters of the selected catheter electrode model candidates in the second frame using Powell's method.

13. The method of claim 1, wherein the step of initializing a catheter electrode model in a first frame of a fluoroscopic image sequence based on input locations of a plurality of CS catheter electrodes in the first frame comprises:

decomposing the plurality of CS catheter electrodes into multiple parts; and initializing separate catheter electrode models in the first frame for the multiple parts, wherein the parts are ordered from a first part to a last part, and wherein the catheter electrode model initialized in the first frame comprises the separate catheter electrode models initialized for the multiple parts.

14. The method of claim 13, wherein the step of tracking the catheter electrode model in a second frame of the fluoroscopic image sequence comprises:

tracking the catheter electrode model for the first part in the second frame based on the electrode position candidates detected using the at least one trained electrode detector;

sequentially tracking the catheter electrode model for each remaining part in order from the first part to the last part in the second frame based on the tracked catheter electrode model for the previous part; and detecting a first combined catheter electrode model of all of the parts in the second frame based on the sequential tracking of the catheter electrode models from the first part to the last part.

15. The method of claim 14, wherein the step of sequentially tracking the catheter electrode model for each remaining part in order from the first part to the last part in the second frame based on the tracked catheter electrode model for the previous part comprises:

generating catheter electrode model candidates for a current part in the second frame based on a position of a last electrode in a catheter electrode model candidate selected for the previous part; and selecting one of the generated catheter electrode model candidates for the current part in the second frame based on probability scores of the catheter electrode model candidates for the current part.

16. The method of claim 14, wherein the step of tracking the catheter electrode model in a second frame of the fluoroscopic image sequence further comprises:

tracking the catheter electrode model for the last part in the second frame based on the electrode position candidates detected using the at least one trained electrode detector;

sequentially tracking the catheter electrode model for each remaining part in reverse order from the last part to the first part in the second frame based on the tracked catheter electrode model for the previously tracked part; and detecting a second combined catheter electrode model of all of the parts in the second frame based on the sequential tracking of the catheter electrode models in reverse order from the last part to the first part; and selecting one of the first combined catheter electrode model and the second combined catheter electrode model having the highest probability value.

17. An apparatus for detecting and tracking coronary sinus (CS) catheter electrodes in a fluoroscopic image sequence, comprising:

means for initializing a catheter electrode model in a first frame of a fluoroscopic image sequence based on input locations of a plurality of CS catheter electrodes in the first frame, wherein the catheter electrode model in the first frame comprises a plurality of template points corresponding to locations of the CS catheter electrodes in the first frame; and means for tracking the catheter electrode model in a second frame of the fluoroscopic image, comprising:

means for detecting electrode position candidates in a second frame of the fluoroscopic image sequence using at least one trained electrode detector;

means for generating catheter electrode model candidates in the second frame based on the detected electrode position candidates and the catheter electrode model initialized in the first frame by translating each of the plurality of template points of the catheter electrode model initialized in the first frame to each of the detected electrode position candidates in the second frame;

means for calculating a probability score for each of the catheter electrode model candidates in the second frame; and means for selecting one of the catheter electrode model candidates in the second frame based on the probability score, wherein the selected catheter electrode model candidate provides locations of the plurality of CS catheter electrodes in the second frame.

18. The apparatus of claim 17, wherein the means for initializing a catheter electrode model in a first frame of a fluoroscopic image sequence based on input locations of a plurality of CS catheter electrodes in the first frame comprises:

means for storing coordinates of the template points based on the plurality of CS catheter electrodes in the first frame and intensity information corresponding to template points based on the plurality of CS catheter electrodes in the first frame.

19. The apparatus of claim 17, wherein the means for initializing a catheter electrode model in a first frame of a fluoroscopic image sequence based on input locations of a plurality of CS catheter electrodes in the first frame comprises:

means for determining a number of CS catheter electrodes in the first frame; and means for decomposing the plurality of CS catheter electrodes into multiple parts if the number of CS catheter electrodes in the first frame is greater than a threshold; and means for initializing separate catheter electrode models in the first frame for the multiple parts, wherein the catheter electrode model initialized in the first frame comprises the separate catheter electrode models initialized for the multiple parts.

20. The apparatus of claim 19, wherein the means for decomposing the plurality of CS catheter electrodes into multiple parts comprises:

means for splitting the CS catheter electrodes into multiple parts based on curvature of a spline representing the CS catheter.

21. The apparatus of claim 17, wherein the means for detecting electrode position candidates in a second frame of the fluoroscopic image sequence using at least one trained electrode detector comprises:

means for detecting a first set of electrode position candidates in the second frame using a first trained electrode detector;

means for detecting a second set of electrode position candidates by pruning the first set of electrode position candidates using a second trained electrode detector; and means for clustering the second set of electrode position candidates using non-maximal suppression.

22. The apparatus of claim 17, wherein the means for generating catheter electrode model candidates in the second frame based on the detected electrode position candidates and the catheter electrode model initialized in the first frame by translating each of the plurality of template points of the catheter electrode model initialized in the first frame to each of the detected electrode position candidates in the second frame comprises:

means for generating a plurality of catheter electrode model hypotheses by translating each of the plurality of template points of the catheter electrode model initialized in the first frame to each of the detected electrode position candidates in the second frame; and means for generating the plurality of catheter electrode model candidates in the second frame by varying affine parameters for each of the plurality of catheter electrode model hypotheses using the respective detected electrode position candidate as an affine transformation center.

23. The apparatus of claim 17, wherein the means for calculating a probability score for each of the catheter electrode model candidates in the second frame comprises:

means for calculating a probability score based on a first probability score and a second probability score, wherein the first probability score is calculated by normalized cross correlation between intensity values of electrodes in the second frame identified by the respective catheter electrode model candidate and the intensity values of the electrodes in the first frame identified by the catheter electrode model, and the second probability score is calculated based on detection scores of the electrodes identified by the respective catheter electrode model candidate determined by the at least one trained electrode detector.

24. The apparatus of claim 17, wherein the means for selecting one of the catheter electrode model candidates based on the probability score comprises:

means for selecting a number of catheter electrode model candidates in the second frame based on the probability scores calculated for the catheter electrode model candidates in the second frame;

means for refining affine parameters of the selected catheter electrode model candidates in the second frame to locally maximize the probability scores; and means for selecting the catheter electrode model candidate in the second frame having the highest locally maximized probability score.

25. The apparatus of claim 17, wherein the means for initializing a catheter electrode model in a first frame of a fluoroscopic image sequence based on input locations of a plurality of CS catheter electrodes in the first frame comprises:

means for decomposing the plurality of CS catheter electrodes into multiple parts; and means for initializing separate catheter electrode models in the first frame for the multiple parts, wherein the parts are ordered from a first part to a last part, and wherein the catheter electrode model initialized in the first frame comprises the separate catheter electrode models initialized for the multiple parts.

26. The apparatus of claim 25, wherein the means for tracking the catheter electrode model in a second frame of the fluoroscopic image sequence comprises:

means for tracking the catheter electrode model for the first part in the second frame based on the electrode position candidates detected using the at least one trained catheter electrode detector;

means for sequentially tracking the catheter electrode model for each remaining part in order from the first part to the last part in the second frame based on the tracked catheter electrode model for the previous part; and means for detecting a first combined catheter electrode model of all of the parts in the second frame based on the sequential tracking of the catheter electrode models from the first part to the last part.

27. The apparatus of claim 25, wherein the means for tracking the catheter electrode model in a second frame of the fluoroscopic image sequence further comprises:

means for tracking the catheter electrode model for the last part in the second frame based on the electrode position candidates detected using the at least one trained electrode detector;

means for sequentially tracking the catheter electrode model for each remaining part in reverse order from the last part to the first part in the second frame based on the tracked catheter electrode model for the previously tracked part; and means for detecting a second combined catheter electrode model of all of the parts in the second frame based on the sequential tracking of the catheter electrode models in reverse order from the last part to the first part; and means for selecting one of the first combined catheter electrode model and the second combined catheter electrode model having the highest probability value.

28. A non-transitory computer readable medium encoded with computer executable instructions for detecting and tracking coronary sinus (CS) catheter electrodes in a fluoroscopic image sequence, the computer executable instructions defining steps comprising:

initializing a catheter electrode model in a first frame of a fluoroscopic image sequence based on input locations of a plurality of CS catheter electrodes in the first frame, wherein the catheter electrode model in the first frame comprises a plurality of template points corresponding to locations of the CS catheter electrodes in the first frame; and tracking the catheter electrode model in a second frame of the fluoroscopic image sequence by:

detecting electrode position candidates in a second frame of the fluoroscopic image sequence using at least one trained electrode detector;

generating catheter electrode model candidates in the second frame based on the detected electrode position candidates and the catheter electrode model initialized in the first frame by translating each of the plurality of template points of the catheter electrode model initialized in the first frame to each of the detected electrode position candidates in the second frame;

calculating a probability score for each of the catheter electrode model candidates in the second frame; and selecting one of the catheter electrode model candidates in the second frame based on the probability score, wherein the selected catheter electrode model candidate provides locations of the plurality of CS catheter electrodes in the second frame.

29. The non-transitory computer readable medium of claim 28, wherein the computer executable instructions defining the step of initializing a catheter electrode model in a first frame of a fluoroscopic image sequence based on input locations of a plurality of CS catheter electrodes in the first frame comprise computer executable instructions defining the step of:

storing coordinates of the template points based on the plurality of CS catheter electrodes in the first frame and intensity information corresponding to template points based on the plurality of CS catheter electrodes in the first frame.

30. The non-transitory computer readable medium of claim 28, wherein the computer executable instructions defining the step of initializing a catheter electrode model in a first frame of a fluoroscopic image sequence based on input locations of a plurality of CS catheter electrodes in the first frame comprise computer executable instructions defining the steps of:

determining a number of CS catheter electrodes in the first frame; and if the number of CS catheter electrodes in the first frame is greater than a threshold, decomposing the plurality of CS catheter electrodes into multiple parts, and initializing separate catheter electrode models in the first frame for the multiple parts, wherein the catheter electrode model initialized in the first frame comprises the separate catheter electrode models initialized for the multiple parts.

31. The non-transitory computer readable medium of claim 30, wherein the computer executable instructions defining the step of decomposing the plurality of CS catheter electrodes into multiple parts comprise computer executable instructions defining the step of:

splitting the CS catheter electrodes into multiple parts based on curvature of a spline representing the CS catheter.

32. The non-transitory computer readable medium of claim 28, wherein the computer executable instructions defining the step of detecting electrode position candidates in a second frame of the fluoroscopic image sequence using at least one trained electrode detector comprise computer executable instructions defining the steps of:

detecting a first set of electrode position candidates in the second frame using a first trained electrode detector;

detecting a second set of electrode position candidates by pruning the first set of electrode position candidates using a second trained electrode detector; and clustering the second set of electrode position candidates using non-maximal suppression.

33. The non-transitory computer readable medium of claim 28, wherein the computer executable instructions defining the step of generating catheter electrode model candidates in the second frame based on the detected electrode position candidates and the catheter electrode model initialized in the first frame by translating each of the plurality of template points of the catheter electrode model initialized in the first frame to each of the detected electrode position candidates in the second frame comprise computer executable instructions defining the steps of:

generating a plurality of catheter electrode model hypotheses by translating each of the plurality of template points of the catheter electrode model initialized in the first frame to each of the detected electrode position candidates in the second frame; and generating the plurality of catheter electrode model candidates in the second frame by varying affine parameters for each of the plurality of catheter electrode model hypotheses using the respective detected electrode position candidate as a transformation center.

34. The non-transitory computer readable medium claim 28, wherein the computer executable instructions defining the step of calculating a probability score for each of the catheter electrode model candidates in the second frame comprise computer executable instructions defining the steps of:

calculating a probability score based on a first probability score and a second probability score, wherein the first probability score is calculated by normalized cross correlation between intensity values of template points in the second frame identified by the respective catheter electrode model candidate and the intensity values of the template points in the first frame identified by the catheter electrode model, and the second probability score is calculated based on detection scores of the electrodes identified by the respective catheter electrode model candidate determined by the at least one trained electrode detector.

35. The non-transitory computer readable medium of claim 28, wherein the computer executable instructions defining the step of selecting one of the catheter electrode model candidates in the second frame based on the probability score comprise computer executable instructions defining the steps of:

selecting a number of catheter electrode model candidates in the second frame based on the probability scores calculated for the catheter electrode model candidates in the second frame;

refining affine parameters of the selected catheter electrode model candidates in the second frame to locally maximize the probability scores; and selecting the catheter electrode model candidate in the second frame having the highest locally maximized probability score.

36. The non-transitory computer readable medium of claim 28, wherein the computer executable instructions defining the step of initializing a catheter electrode model in a first frame of a fluoroscopic image sequence based on input locations of a plurality of CS catheter electrodes in the first frame comprise computer executable instructions defining the steps of:

decomposing the plurality of CS catheter electrodes into multiple parts; and initializing separate catheter electrode models in the first frame for the multiple parts, wherein the parts are ordered from a first part to a last part, and wherein the catheter electrode model initialized in the first frame comprises the separate catheter electrode models initialized for the multiple parts.

37. The non-transitory computer readable medium of claim 36, wherein the computer executable instructions defining the step of tracking the catheter electrode model in a second frame of the fluoroscopic image sequence comprise computer executable instructions defining the steps of:

tracking the catheter electrode model for the first part in the second frame based on the electrode position candidates detected using the at least one trained electrode detector;

sequentially tracking the catheter electrode model for each remaining part in order from the first part to the last part in the second frame based on the tracked catheter electrode model for the previous part; and detecting a first combined catheter electrode model of all of the parts based in the second frame on the sequential tracking of the catheter electrode models from the first part to the last part.

38. The non-transitory computer readable medium of claim 37, wherein the computer executable instructions defining the step of tracking the catheter electrode model in a second frame of the fluoroscopic image sequence further comprise computer executable instructions defining the steps of:

tracking the catheter electrode model for the last part in the second frame based on the electrode position candidates detected using the at least one trained electrode detector;

sequentially tracking the catheter electrode model for each remaining part in reverse order from the last part to the first part in the second frame based on the tracked catheter electrode model for the previously tracked part;

detecting a second combined catheter electrode model of all of the parts in the second frame based on the sequential tracking of the catheter electrode models in reverse order from the last part to the first part; and selecting one of the first combined catheter electrode model and the second combined catheter electrode model having the highest probability value.

* * * * *